(12) United States Patent
Lorenz et al.

(10) Patent No.: US 11,246,564 B2
(45) Date of Patent: Feb. 15, 2022

(54) ULTRASOUND DIAGNOSIS APPARATUS

(71) Applicant: KONINKLIJKE PHILIPS N. V., Eindhoven (NL)

(72) Inventors: Cristian Lorenz, Hamburg (DE); Tobias Klinder, Uelzen (DE); Irina Waechter-Stehle, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 349 days.

(21) Appl. No.: 16/329,257

(22) PCT Filed: Sep. 1, 2017

(86) PCT No.: PCT/EP2017/071998
§ 371 (c)(1),
(2) Date: Feb. 28, 2019

(87) PCT Pub. No.: WO2018/042008
PCT Pub. Date: Mar. 8, 2018

(65) Prior Publication Data
US 2019/0183455 A1 Jun. 20, 2019

(30) Foreign Application Priority Data
Sep. 1, 2016 (EP) .................................. 16186862

(51) Int. Cl.
*A61B 8/08* (2006.01)

(52) U.S. Cl.
CPC ............ *A61B 8/0866* (2013.01); *A61B 8/483* (2013.01); *A61B 8/52* (2013.01); *A61B 8/5215* (2013.01); *A61B 8/5223* (2013.01); *A61B 8/5207* (2013.01)

(58) Field of Classification Search
CPC ....... A61B 8/0866; A61B 8/5223; A61B 8/52; A61B 8/483; A61B 8/5215; A61B 8/5207
See application file for complete search history.

(56) References Cited

U.S. PATENT DOCUMENTS

| 8,257,261 B2 * | 9/2012 | Kawae | ................. A61B 8/0866 600/443 |
| 9,216,007 B2 | 12/2015 | Lee | |
| 10,586,332 B2 * | 3/2020 | Hu | .......................... G06T 19/00 |

(Continued)

FOREIGN PATENT DOCUMENTS

| CN | 102048557 A | 5/2011 |
| CN | 102151149 A | 8/2011 |

(Continued)

OTHER PUBLICATIONS

International Search Report and Written Opinion for International Application No. PCT/EP2017/071998, dated Dec. 12, 2017, 12 pages.

*Primary Examiner* — Boniface Ngathi

(57) ABSTRACT

The present invention relates to an ultrasound diagnosis apparatus (10), in particular for analyzing a fetus (62). An ultrasound data interface (66) is configured to receive 3D (three dimensional) ultrasound data from an object (12). The ultrasound diagnosis apparatus further comprises a measurement unit (70) for measuring anatomical structures of the object based on the segmentation data and a calculation unit (72) configured to calculate at least one biometric parameter based on the 3D ultrasound data.

20 Claims, 5 Drawing Sheets

(56) References Cited

U.S. PATENT DOCUMENTS

| | | | |
|---|---|---|---|
| 2006/0135855 A1 | 6/2006 | Alsafadi et al. | |
| 2007/0081705 A1 | 4/2007 | Carneiro et al. | |
| 2009/0030314 A1* | 1/2009 | Kawae | A61B 8/0866 600/443 |
| 2012/0065512 A1* | 3/2012 | Hamada | A61B 8/14 600/443 |
| 2012/0101383 A1 | 4/2012 | Hyun | |
| 2013/0072797 A1* | 3/2013 | Lee | G01S 15/8993 600/443 |
| 2013/0173175 A1 | 7/2013 | Jung et al. | |
| 2014/0148696 A1 | 5/2014 | Yoo | |
| 2015/0049932 A1* | 2/2015 | Moulis | G06T 7/30 382/131 |
| 2016/0199036 A1* | 7/2016 | Pelissier | A61B 8/466 600/440 |

FOREIGN PATENT DOCUMENTS

| | | |
|---|---|---|
| EP | 2624211 A1 | 8/2013 |
| EP | 2982306 A1 | 2/2016 |
| WO | 2012042808 A1 | 4/2012 |

\* cited by examiner

ULTRASOUND DIAGNOSIS APPARATUS

This application is the U.S. National Phase application under 35 U.S.C. § 371 of International Application No. PCT/EP2017/071998 filed on Sep. 1, 2017, which claims the benefit of European Application Serial No. 16186862.5, filed on Sep. 1, 2016. These applications are hereby incorporated by reference herein.

FIELD OF THE INVENTION

The present invention relates to an ultrasound diagnosis apparatus, in particular for analyzing a fetus. The present invention further relates to an ultrasound diagnosis method, in particular for analyzing a fetus. The present invention further relates to an ultrasound imaging apparatus including a graphical user interface and an ultrasound diagnosis apparatus according to the present invention for displaying calculation results of at least one calculated biometric parameter of the analyzed object. The present finally relates to a computer program to carry out the steps of the method according to the present invention.

BACKGROUND OF THE INVENTION

Ultrasound imaging systems are generally known for examination of anatomical features in human patients. In particular, ultrasound imaging systems and ultrasound diagnosis systems are used for prenatal screening examination of a fetus including measuring biometrics of the fetus as e.g. disclosed by US 2013/0173175 A1.

The fetal ultrasound is the modality of choice for fetus screening, diagnosis and the estimation of the gestational age. Current procedures as disclosed by the above-mentioned document US 2013/0173175 A1 are mainly based on two dimensional ultrasound. However, ultrasound based biometric measurements are error prone and time-consuming and usually limited to the number of actually taken measurements. Assuming a normal case, the gestational age can be estimated by just one measurement, e.g. the head circumference, the femur length of the like. For screening, biometrical measurements are typically individual performed for a given task, e.g. the diameter of the cerebellum may be measured to detect brain development abnormalities. These measurements however, lead to situations where abnormalities are overlooked, or where the lack of accuracy of biometric measurements remains undetected.

Automated analysis of ultrasound images however enables the execution of a large set of measurements in a short time. The images are readily available in the system for further processing, while the ultrasound measurements have to be inactively executed and entered into the system. The ability to perform automated biometric measurements the head increases the efficiency of fetal screening. At the same time, it is not always clear for the operator if the measurement can be trusted. Due to the redundancy contained in a larger set of measurements it is possible to detect disagreement based on a certain deviation threshold that e.g. relates to typical modality dependent measurement accuracy. In case of a disagreement at this stage, it is unclear if it is caused by a measurement error or by an abnormality. The operator is guided to outsell this question by a display of a disagreeing measurement on top of the image showing the related anatomical structure.

However, the ultrasound diagnosis systems available do not have an error detection system which indicates to the operator whether abnormalities of the detected biometric parameter is correct if it deviates from expected biometric parameter.

US 2007/0081705 A1 discloses a method for segmenting and measuring anatomical structures in fetal ultrasound images including the steps of providing a digitized ultrasound image of a fetus comprising a plurality of intensities corresponding to a domain of points on a 3D grid, providing a plurality of classifiers trained to detect anatomical structures in said image of said fetus, and segmenting and measuring an anatomical structure using said image classifiers by applying said elliptical contour classifiers to said fetal ultrasound image, wherein a plurality of 2D contours characterizing said anatomical structure are detected. The anatomical structure measurement can be combined with measurement of another anatomical structure to estimate gestational age of the fetus.

EP 2 624 211 A1 discloses an image processing apparatus including: a data acquisition device for acquiring image data of a subject including a target bone; and a data processor for acquiring binary image data by performing thresholding based on the image data, segmenting the binary image data into a plurality of segments by labeling, determining one of the plurality of segments as a target image based on image characteristics of the target bone, and measuring a length of the target bone based on the target image.

EP 2 982 306 A1 discloses an ultrasound diagnosis apparatus including: a data acquisition unit configured to acquire volume data for a head of an object; an image processor configured to detect a mid-sagittal plane (MSP) from the volume data, generate an MSP image corresponding to the MSP, detect at least one measurement plane based on the MSP, and generate at least one measurement plane image corresponding to the at least one measurement plane; and a display configured to display the MSP image and the at least one measurement plane image on a single screen.

SUMMARY OF THE INVENTION

It is an object of the present invention to provide an improved ultrasound diagnosis apparatus, which comprises an automated error detection for calculated and measured biometric parameters, and which provides an improved accuracy of the provided ultrasound detection. It is a further object of the present invention to provide a corresponding method, a corresponding ultrasound imaging apparatus and a corresponding computer program for implementing such a method.

In a first aspect of the present invention, an ultrasound diagnosis apparatus, in particular for analyzing an object is presented, comprising:

an ultrasound data interface configured to receive 3D (three dimensional) ultrasound data from the object, a plane extraction unit configured to provide 2D ultrasound planes based on the 3D ultrasound data, a segmentation unit for segmenting anatomical structures of the object in the 2D ultrasound planes and for providing segmentation data of the anatomical structures;

a measurement unit for measuring the anatomical structures of the object based on the segmentation data of the anatomical structures, and a calculation unit configured to calculate at least one biometric parameter based on the measured anatomical structures of the object.

In a further aspect of the present invention an ultrasound diagnosis method, in particular for analyzing an object is presented, comprising the steps of:

receiving 3D (three dimensional) ultrasound data at an ultrasound data interface from the object, extracting 2D ultrasound planes based on the 3D ultrasound data;

segmenting anatomical structures of the object in the 2D ultrasound planes to provide segmentation data of the anatomical structures;

measuring anatomical structures of the object based on the segmentation data of the anatomical structures, and calculating at least one biometric parameter based on the measured anatomical structures of the object.

In a further aspect of the present invention, an ultrasound imaging apparatus, in particular for imaging an object, is presented, comprising:

a graphical user interface, in particular a display unit configured to display ultrasound image data, and an ultrasound diagnosis apparatus as claimed in claim 1 for analyzing the object, wherein the graphical user interface is adapted to display the calculation results of the at least one biometric parameter.

In a still further aspect of the present invention, a computer is presented comprising program code means for causing a computer to carry out to the steps of the above-mentioned method when said computer program is carried out on a computer.

Preferred embodiments of the invention are defined in the dependent claims. It shall be understood that the claim method has similar and/or identical preferred embodiments as the claimed device and as defined in the dependent claims.

The present invention is based on the idea to utilize three dimensional ultrasound data captured from the object and to provide automatically extracted two dimensional data planes in order to determine biometric parameters for measuring certain biometric components of the object, in particular the gestational age of the fetus. Due to the measurement of the object by three dimensional (3D) ultrasound systems, the exposure of the irradiation in particular of the fetus is reduced so that the health of the object is not affected compared to CT image based 3D data. Consequently, the ultrasound diagnosis apparatus can be utilized to determine critical biometric 3D parameters while the health of the object is not affected by the ultrasound radiation.

In a preferred embodiment, the ultrasound diagnosis apparatus further comprises a data interface configured to receive biometric data for calculating the at least one biometric parameter. This is a possibility to provide reference data to compare the calculated biometric parameter with prior calculated parameters or with biometric parameters of the literature so that the technical effort for determining a wrong biometric parameter is reduced.

The ultrasound diagnosis apparatus further comprises a segmentation unit for segmenting anatomical structures of the object in the ultrasound data and for providing segmentation data of the anatomical structures, wherein the measurement unit is provided for measuring anatomical structures of the object based on the segmentation data if this is required by the sub-sequent measurement unit, if not the segmentation unit can be omitted. The segmentation unit gives a possibility of improving the measurement results of the anatomical structures and the determination of the at least one biometric parameter.

In a further preferred embodiment, the biometric data comprises predefined model-based segmentation data. This is a possibility to reduce the technical effort for determining an error of the biometric parameter based on the segmentation data, since the biometric parameter is based on model-based segmentation data.

The ultrasound diagnosis apparatus further comprises a plane extraction unit configured to provide 2D (two dimensional) ultrasound planes based on the 3D ultrasound data, wherein the segmentation unit is configured to segment the anatomical structures based on the 2D ultrasound planes. This is a possibility to reduce the technical effort, since the segmentation of the anatomical structures based on the 2D ultrasound planes can be technically less complex than the segmentation of 3D volume image data.

In a further preferred embodiment, the measurement unit is configured to measure the at least one biometric parameter based on a direct measurement (without an explicit prior segmentation), e.g. using machine learning methods such as neural network based approaches. This In a further preferred embodiment, the measurement unit is configured to measure the at least one biometric parameter based on a measurement algorithm. This is a possibility to further reduce the complexity of the calculation of the biometric parameter.

It is further preferred, if the algorithm is preselected and stored in a memory of the ultrasound diagnosis apparatus. This is a possibility to utilize a predefined algorithm by default in order to provide a first estimation of the biometric parameter which utilize the system in addition of flexibility and a simplicity for the operator to handle the apparatus.

In a further preferred embodiment, the measurement algorithm is preselected by the user. This is a possibility to further simplify the ultrasound diagnosis apparatus and the calculated biometric parameter, since the user is familiar with the measurement algorithm of the at least one biometric parameter.

In a further preferred embodiment, the measurement algorithm is selected based on the calculated at least one biometric parameter. This is a possibility to iteratively improve the calculation of the at least one biometric parameter.

In a further preferred embodiment, the measurement unit is configured to measure the anatomical structures based on different measurement algorithms. This is a possibility to automatically adapt the measurement algorithm and to iteratively reach an optimal measurement algorithm to determine the current biometric parameter.

In a further preferred embodiment, the measurement unit is configured to measure the anatomical structures based on different measurement algorithms. This is a possibility to compare the measurement results of the different measurement algorithms in order to find the best measurement algorithm to determine the biometric parameter to be calculated.

In a further preferred embodiment, the measurement unit is configured to measure the 3D image data based on different anatomical structures of the object. This is a possibility to correlate a set of measurements of different measurements of e.g. a left and a right anatomical feature e.g. of the left and the right thighbone (femur). This is a further possibility to provide a biometry accuracy estimation based on a set of ultrasound measurements.

In a further preferred embodiment, the calculation unit is configured to calculate a cross correlation of the segmentation data based on different ultrasound data in order to determine errors in measurements from the given 3D ultrasound data. This is a possibility to determine errors in the measured ultrasound data with low technical effort, since different ultrasound data is utilized to compare the biometric parameter and to calculate a cross correlation.

In a further preferred embodiment, the calculation unit is configured to calculate a cross correlation of the segmentation data based on different measurement algorithms in order to determine deviation in the 3D ultrasound data. This is a possibility to determine erroneous ultrasound data with low technical effort, since the cross correlation of the different measurement algorithms can be compared with low technical effort.

In a further preferred embodiment, the measurement unit is configured to determine errors based on a cross correlation of different algorithms.

In a further preferred embodiment, the ultrasound diagnosis apparatus further comprises a graphical user interface, in particular a display unit, e.g. a touchscreen which is configured to display the calculation results of the at least one biometric parameter and which can be utilized as input unit to input instructions of the user. This is a possibility to present the measured and calculated biometric parameter to the user and a possible error of the calculated parameter so that the handling effort of the ultrasound diagnosis apparatus can be reduced.

In a further embodiment, the measurement unit is configured to perform a plurality of different biometric measurements of the anatomical structures of the object based on the segmentation data of the anatomical structures, and wherein the calculation unit is configured to calculate a parameter value of the at least one biometric parameter based on each of the plurality of different biometric measurements, separately.

In a further embodiment, each of the plurality of different biometric measurements performed by the measurement unit (i) evaluates a different biometric measure of the object, (ii) is performed based on a different measurement algorithm, and/or (iii) is performed based on segmentation data derived from a different 3D ultrasound data set.

In a further embodiment, the calculation unit is configured to calculate a cross-correlation of the parameter values calculated based on each of the plurality of different biometric measurements.

In a further embodiment, the calculation unit is configured to estimate an accuracy of the calculation of the at least one biometric parameter if the calculated cross-correlation is above a predefined correlation threshold.

In a further embodiment, the calculation unit is configured to calculate a further parameter value of the at least one biometric parameter based on a further biometric measurement performed by the measurement unit if the calculated cross-correlation is below a predefined correlation threshold.

In a further embodiment, the calculation unit is configured to compare the further parameter value with the parameter values calculated based on each of the plurality of different biometric measurements and to derive a confidence value based on said comparison.

As mentioned above, the three dimensional ultrasound data can improve the accuracy of the measurements of the object in order to improve the calculation results of the at least one biometric parameter to improve the diagnosis of the ultrasound diagnosis apparatus in general. Further, due to the ultrasound image data taken from the object, the radiation exposure of the object can be reduced, so that the stress for the object can be reduced.

Further, due to different calculation algorithms and different data bases, the technical effort to determine an error in the captured ultrasound data can be reduced.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before referring to the medical ultrasound diagnosis apparatus 10 according to an aspect of the present invention, the basic principles of an ultrasound system 100 shall be explained with reference to FIGS. 1 and 2.

Figure 1:
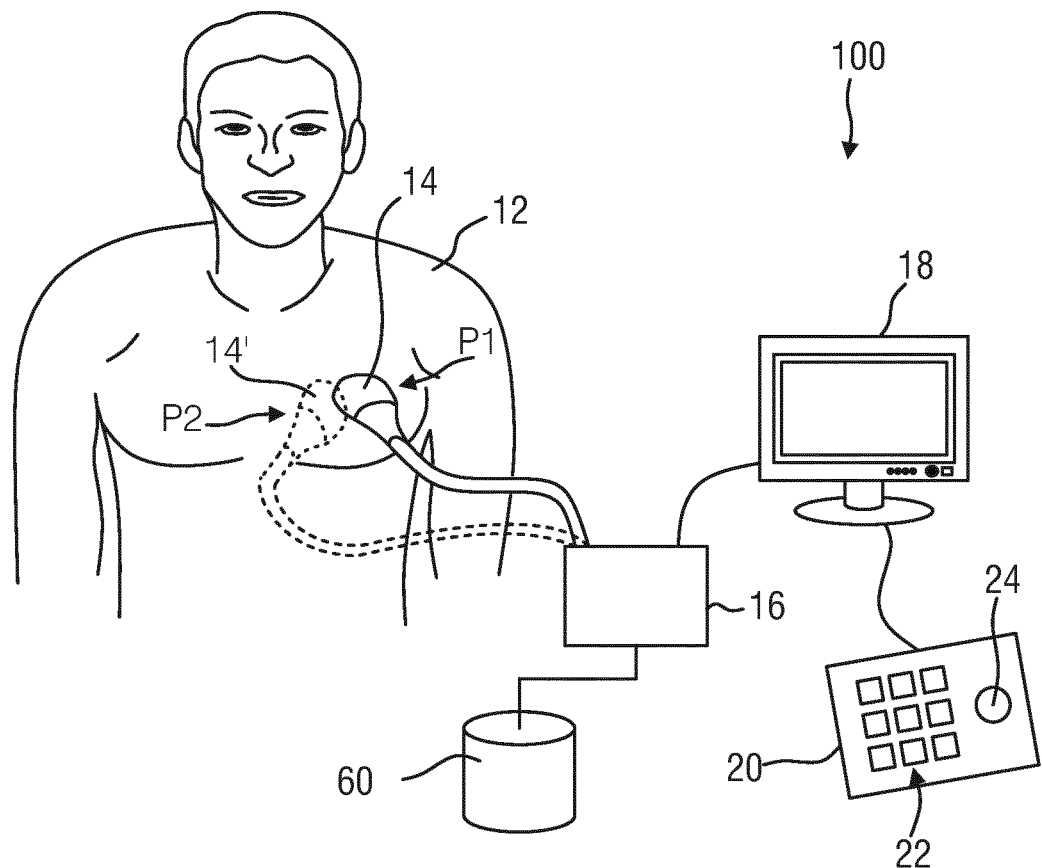
FIG. 1 shows a schematic representation of an ultrasound imaging system in use to scan a part of a patient's body.

FIG. 1 shows a schematic illustration of an ultrasound system 100, in particular a medical three-dimensional (3D) ultrasound imaging system. The ultrasound imaging system 100 is applied to inspect a volume of an anatomical site, in particular an anatomical site of a patient 12 over time. The ultrasound system 100 comprises an ultrasound probe 14 having at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. The transducer elements are preferably arranged in a two-dimensional array, in particular for providing a multi-planar or three-dimensional image.

A particular example for a three-dimensional ultrasound system which may be the CX40 Compact Xtreme ultrasound system sold by the applicant, in particular together with a X6-1 or X7-2t TEE transducer of the applicant or another transducer using the xMatrix technology of the applicant. In general, matrix transducer systems as found on Philips iE33 systems or mechanical 3D/4D transducer technology as found, for example, on the Philips iU22 and HD15 systems may be applied in conjunction with the current invention.

A 3D ultrasound scan typically involves emitting ultrasound waves that illuminate a particular volume within a body, which may be designated as target volume or volumetric region. This can be achieved by emitting ultrasound waves at multiple different angles. A set of volume data is then obtained by receiving and processing reflected waves. The set of volume data is a representation of the target volume within the body over time. Since time is usually denoted as fourth dimension, such ultrasound system 100 delivering a 3D image sequence over time, is sometimes also referred to a 4D ultrasound imaging system.

It shall be understood that the ultrasound probe 14 may either be used in a non-invasive manner (as shown in FIG. 1) or in an invasive manner as this is usually done in TEE (not explicitly shown). The ultrasound probe 14 may be hand-held by the user of the system, for example medical staff or a physician. The ultrasound probe 14 is applied to the body of the patient 12 so that an image of an anatomical site, in particular an anatomical object of the patient 12 is provided.

Further, the ultrasound system 100 may comprise an image reconstruction unit 16 that controls the provision of a 3D image sequence via the ultrasound system 100. As will be explained in further detail below, the image reconstruction unit 16 may control not only the acquisition of data via the transducer array of the ultrasound probe 14, but also signal and image processing that form the 3D image sequence out of the echoes of the ultrasound beams received by the transducer array of the ultrasound probe 14.

The ultrasound system 100 may further comprise a display 18 for displaying the 3D image sequence to the user. Still further, an input device 20 may be provided that may comprise keys or a keyboard 22 and further inputting devices, for example a trackball 24. The input device 20 might be connected to the display 18 or directly to the image reconstruction unit 16.

Figure 2:
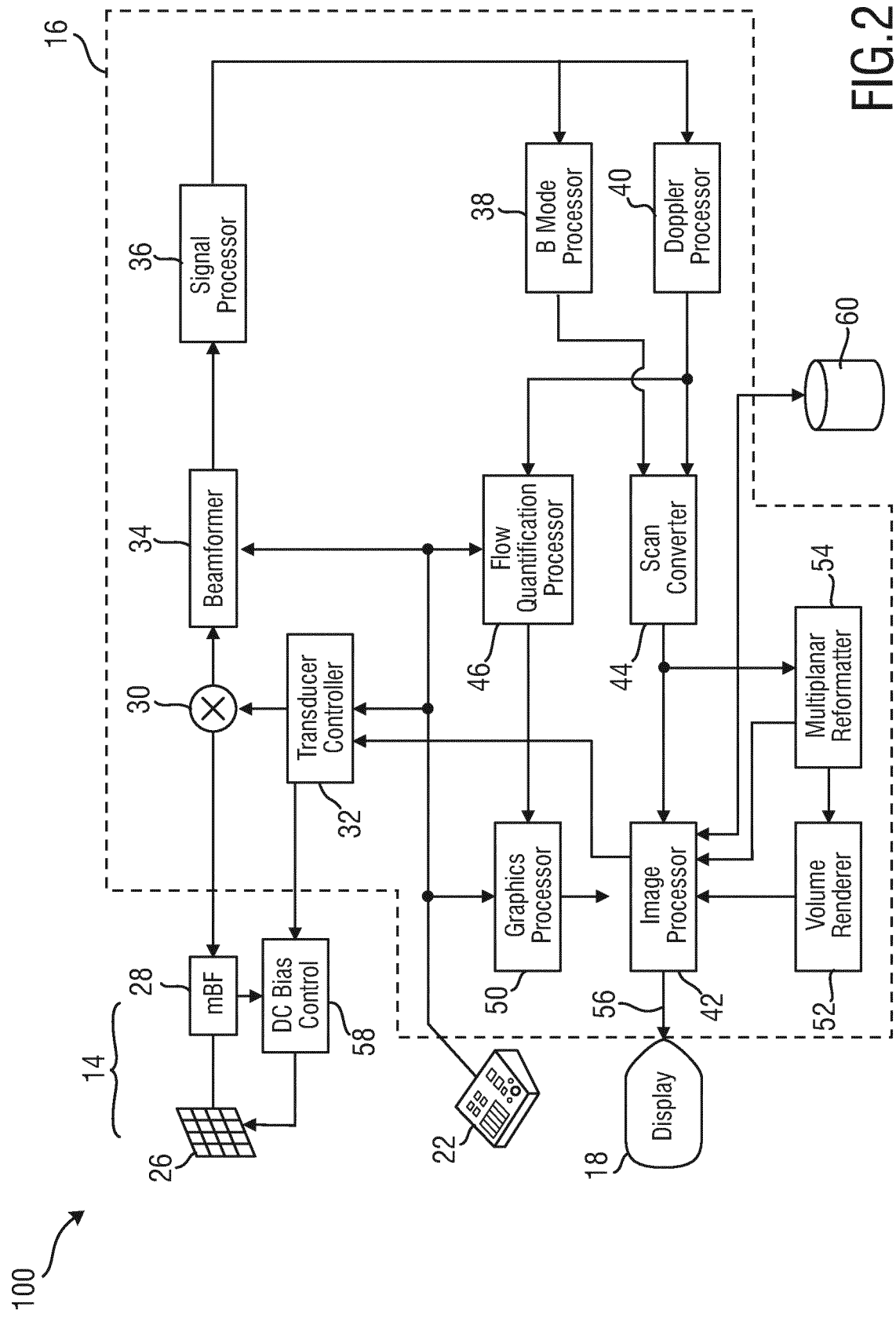
FIG. 2 shows a schematic block diagram of an embodiment of an ultrasound imaging system with an array transducer.

FIG. 2 illustrates a schematic block diagram of the ultrasound system 100. The ultrasound probe 14 may, for example, comprise a CMUT transducer array 26. The transducer array 26 may alternatively comprise piezoelectric transducer elements formed of materials such as PZT or PVDF. The transducer array 26 is a one- or a two-dimensional array of transducer elements capable of scanning in three dimensions for 3D imaging. The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer 28 may be coupled by a probe cable to a transmit/receive (T/R) switch 30 which switches between transmission and reception and protects the main beamformer 34 from high energy transmit signals when a microbeamformer 28 is not used and the transducer array 26 is operated directly by the main beamformer 34. The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for the CMUT array. The DC bias control 58 sets DC bias voltage(s) that are applied to the CMUT cells.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient 12. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.)

The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format, or a pyramidal three dimensional (3D) image. The scan converter 44 can overlay a B mode structural image with colors corresponding to motion at points in the image field with their Doppler-estimated velocities to produce a color Doppler image which depicts the motion of tissue and blood flow in the image field. The multiplanar reformatter 54 will convert echoes which are received from points in a common plane in a volumetric region of the body into an ultrasonic image of that plane, as described in U.S. Pat. No. 6,443,896 (Detmer). A volume renderer 52 converts the echo signals of a 3D data set into a projected 3D image sequence 56 over time as viewed from a given reference point as described in U.S. Pat. No. 6,530,885 (Entrekin et al.). The 3D image sequence 56 is transferred from the scan converter 44, multiplanar reformatter 54, and volume renderer 52 to an image processor 42 for further enhancement, buffering and temporary storage for display on the display 18. In addition to being used for imaging, the blood flow values produced by the Doppler processor 40 and tissue structure information produced by the B mode processor 38 may be transferred to a quantification processor 46. This quantification processor 46 may produce measures of different flow conditions such as the volume rate of blood flow as well as structural measurements such as the sizes of organs and gestational age. The quantification processor 46 may receive input from the user control panel 22, such as the point in the anatomy of an image where a measurement is to be made. Output data from the quantification processor 46 may be transferred to a graphics processor 50 for the reproduction of measurement graphics and values with the image on the display 18. The graphics processor 50 can also generate graphic overlays for display with the ultrasound images. These graphic overlays can contain standard identifying information such as patient name, date and time of the image, imaging parameters, and the like. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system. The user interface 22 may also be coupled to the multiplanar reformatter 54 for selection and control of the planes of multiple multiplanar reformatted (MPR) images which may be used to perform quantified measures in the image field of the MPR images.

Again, it shall be noted that the aforementioned ultrasound system 100 has only been explained as one possible example for an application of the medical ultrasound image processing device 10. It shall be noted that the aforementioned ultrasound system 100 does not have to comprise all of the components explained before. On the other hand, the ultrasound system 100 may also comprise further components, if necessary. Still further, it shall be noted that a plurality of the aforementioned components do not necessarily have to be realized as hardware, but may also be realized as software components. A plurality of the aforementioned components may also be comprised in common entities or even in one single entity and do not all have to be realized as separate entities, as this is schematically shown in FIG. 2.

Figure 3:
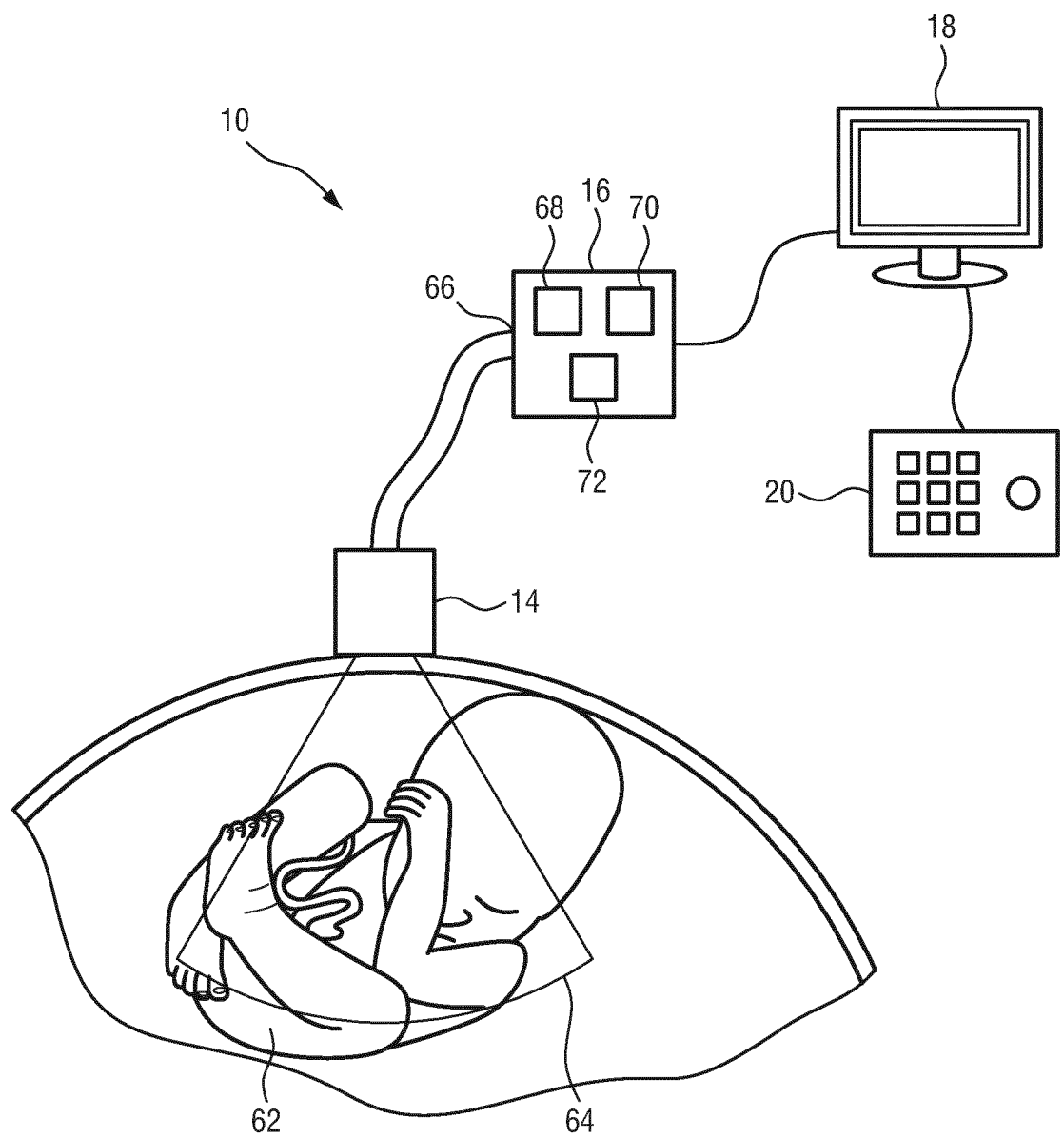
FIG. 3 shows a schematic diagram of the ultrasound imaging apparatus for scanning a fetus.

FIG. 3 shows a schematic view of the ultrasound diagnosis apparatus which is generally denoted by 10. The ultrasound diagnosis apparatus 10 scans by means of the ultrasound probe 14 a fetus, which is generally denoted by 62. The ultrasound probe 14 scans an anatomical site, which forms a region of interest and which is generally denoted by 64. The ultrasound probe 14 is connected to the image reconstruction unit 16 via an ultrasound data interface 66 and which comprises a segmentation unit 68, a measurement unit 70 and a calculation unit 72.

The image reconstruction unit 16 is connected to the display 18 for displaying the results of the ultrasound scan and which is connected to the input device 20 for inputting instructions to control the medical ultrasound diagnosis apparatus 10.

The segmentation unit 68 is provided for segmenting anatomical structures of the fetus 62 in the 3D ultrasound data captured by the ultrasound probe 14 and the segmentation unit 68 provides segmentation data of the anatomical structures of the fetus 62. The measurement unit 72 is provided for measuring the anatomical structures of the fetus 62 based on the segmentation data provided by the segmentation unit 68. The calculation unit 72 is configured to calculate at least one biometric parameter of the fetus 62 based on the segmentation data provided by the segmentation unit 68. Based on the so-determined at least one biometric parameter, different biometric analyses can be performed, in particular the gestational age of the fetus 62 can be calculated based on measured sizes of anatomical structures in the head of the fetus 62.

Figure 4:
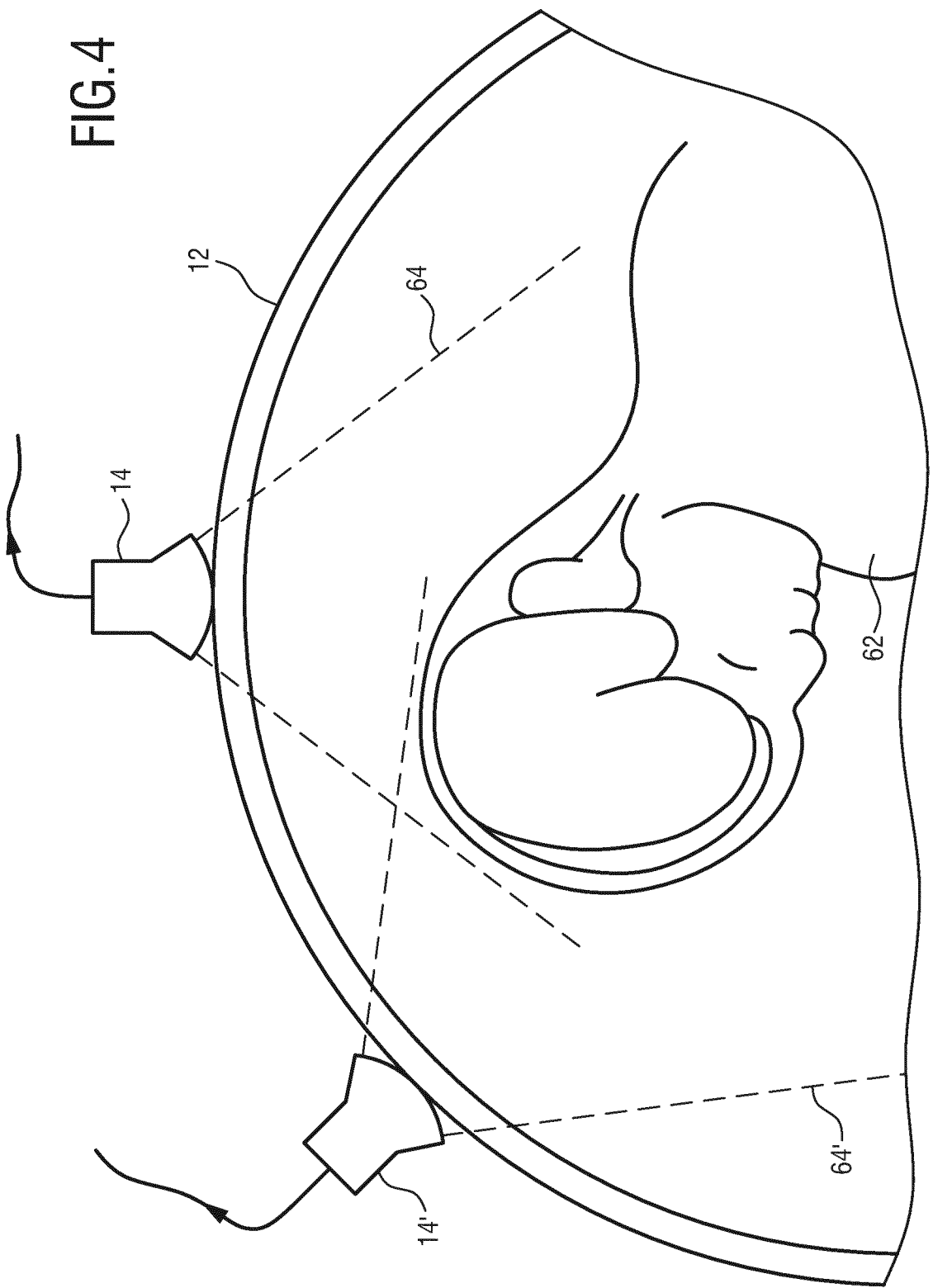
FIG. 4 shows a schematic diagram of the patient to be scanned in two different viewing directions.

FIG. 4 shows a detailed schematic diagram of the object 12 to be scanned by the ultrasound probe 14, wherein in this particular case the object is a fetus 62 to be scanned and to determine a gestational age based on biometric sizes of different individual biometrical parameter within the head of the fetus 62.

In order to measure the biometric parameter, at first a plurality of ultrasound scans are performed at different positions with different regions of interest 64, 64', as shown in FIG. 4 and the scans are provided via the ultrasound data interface 66 to the segmentation unit 68 in order to perform a model-based segmentation followed by a model-based measurement.

In the particular case shown in FIG. 4, a calculation of the gestational age is performed on all different individual biometric measurements, wherein a direct trust correlation of the individual measurements is performed in order to evaluate an agreement between the measurements of the different model-based segmentation measurements. In case of an agreement between the different individual measurements, the accuracy is estimated of the gestational age and all other measurements.

In the case of a disagreement or a miscorrelation between the individual measurements, the measurement unit 72 runs different mathematic algorithms in order to extract the at least one biometric parameter of the different viewing directions and the different biometric measurements captured by the ultrasound probe 14. The measurement unit 72 evaluates similarities between the different biometric measurements and derives a confidence measure based on the different viewing directions 64, 64'.

This is a possibility to rule out measurement errors, to correct errors or to exclude individual measurements in order to achieve correct calculation of the biometric parameter and to achieve a correct calculation of the gestational age of the fetus 62.

If the disagreement between the measurements is persistent, the measurement unit 72 checks the ultrasound data for related abnormalities and guides the operator to assess the respective relevant anatomical structures.

To evaluate the ultrasound measurements, the model-based segmentation and the calculated at least one biometric parameter on the basis of a comparison to prior captured ultrasound images of the same fetus 62 or in comparison to biometric parameters of a different fetus stored e.g. in the memory 60 or in a database can be performed.

Figure 5:
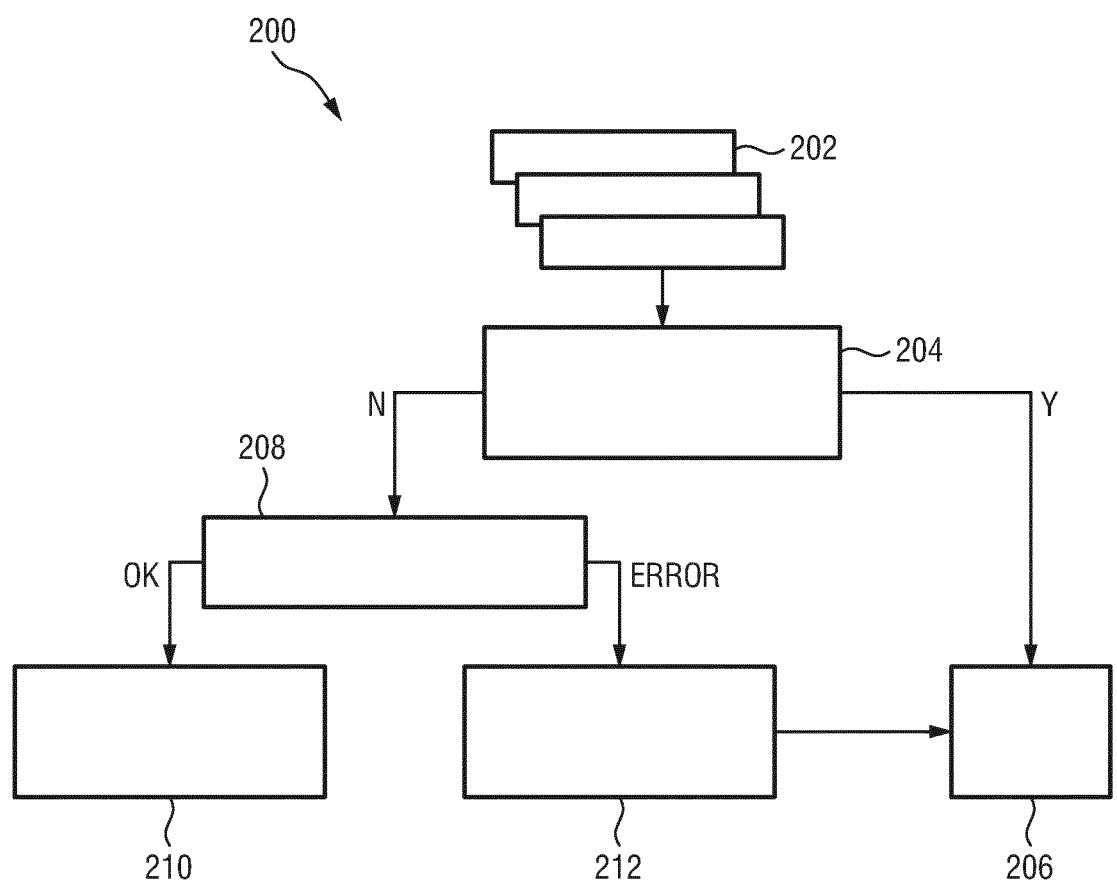
FIG. 5 shows a schematic flow diagram of the ultrasound diagnosis method for analyzing the fetus.

FIG. 5 shows a schematic flow diagram of the ultrasound diagnosis method according to the present invention, which is generally denoted by 200.

At first a plurality of ultrasound measurement of a different region of interests 64, 64' are performed at step 202 At step 204, the calculation unit 72 calculates a correction analysis of the calculated biometric parameter, which is in this case the gestational age via a pairwise correlation. If any agreement between the different biometric parameters of the different viewing directions 64, 64' is achieved, at step 206 a biometric accuracy estimation is performed.

If no agreement can be achieved between the different biometric parameters of the different viewing directions 64, 64' is present, a visual feedback of the conflict measurement can be provided to the user via the display 18 at step 208.

Based on the visual feedback provided in step 208, an assessment of the related abnormalities is performed by the user at step 210 about the amount of disagreement, wherein the crucia anatomy is displayed on the display screen 18.

If an error of the measurement can be detected at step 208, the respective measurement is excluded or the conflict measurement is corrected at step 212. Based on the so-corrected measurement, the biometric accuracy estimation can be performed at step 206.

The biometric accuracy estimation is calculated by the measurement unit 72 via one or a plurality of measurements or calculation algorithms. The measurement algorithm is either preselected by the system itself or by the user and utilized for a first estimation of the biometric parameter. In case of a disagreement of the gestational age, the measurement unit 72 measures the anatomical structures based on different measured algorithms selected by the system itself in order to stepwise achieve a pairwise correlation of the analysis.

The present ultrasound diagnosis apparatus 10 may utilize 3D fetal models in order to determine the anatomical structures of the object 12 and may utilize the measured 3D ultrasound data received from the ultrasound probe 14 directly or may comprise a plane extraction unit within the image reconstruction unit 16, which is configured to provide 2D ultrasound planes based on the 3D ultrasound data so that the segmentation effort is in general reduced.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Ultrasound diagnosis apparatus for analyzing an object, comprising:
   an ultrasound data interface configured to receive 3D ultrasound data from the object; and
   a processor configured to: (i) provide 2D ultrasound planes based on the 3D ultrasound data, (ii) segment anatomical structures of the object in the 2D ultrasound planes to provide segmentation data of the anatomical structures; (iii) measure the anatomical structures of the object based on the segmentation data of the anatomical structures to generate a plurality of different biometric measurements of the anatomical structures, (iv) calculate at least one biometric parameter based on the measured anatomical structures of the object; (v) calculate a parameter value of the at least one biometric parameter based on each of the plurality of different biometric measurements, separately; and (vi) calculate a cross-correlation of the parameter values.

2. Ultrasound diagnosis apparatus as claimed in claim 1, further comprising a data interface configured to receive biometric data for calculating the at least one biometric parameter.

3. Ultrasound diagnosis apparatus as claimed in claim 2, wherein the biometric data comprises predefined model-based segmentation data.

4. Ultrasound diagnosis apparatus as claimed in claim 1, wherein the processor is configured to calculate the at least one biometric parameter based on a measurement algorithm.

5. Ultrasound diagnosis apparatus as claimed in claim 4, wherein the algorithm is preselected and stored in a memory of the ultrasound diagnosis apparatus.

6. Ultrasound diagnosis apparatus as claimed in claim 5, wherein the measurement algorithm is preselected by the user.

7. Ultrasound diagnosis apparatus as claimed in claim 4, wherein the measurement algorithm is selected based on the calculated at least one biometric parameter.

8. Ultrasound diagnosis apparatus as claimed in claim 1, wherein the plurality of different biometric measurements performed by the processor: (i) evaluate different biometric measures of the object, (ii) are performed based on different measurement algorithms, and/or (iii) are performed based on segmentation data derived from different 3D ultrasound data sets.

9. Ultrasound diagnosis apparatus as claimed in claim 1, wherein the processor is configured to estimate an accuracy of the calculation of the at least one biometric parameter if the calculated cross-correlation is above a predefined correlation threshold.

10. Ultrasound diagnosis apparatus as claimed in claim 1, wherein the processor is configured to calculate a further parameter value of the at least one biometric parameter based on a further biometric measurement performed by the processor if the calculated cross-correlation is below a predefined correlation threshold.

11. Ultrasound diagnosis apparatus as claimed in claim 10, wherein the processor is configured to compare the further parameter value with the parameter values calculated based on each of the plurality of different biometric measurements and to derive a confidence value based on said comparison.

12. Ultrasound diagnosis method for analyzing an object, comprising the steps of:
   receiving 3D ultrasound data at an ultrasound data interface from the object; extracting 2D ultrasound planes based on the 3D ultrasound data;
   segmenting an anatomical structure of the object in the 2D ultrasound planes to provide segmentation data of the anatomical structure;
   measuring the anatomical structure of the object based on the segmentation data of the anatomical structure to generate a plurality of different measurements of the anatomical structure;

calculating at least one biometric parameter for each of the plurality of different measurements of the anatomical structure based on the measured anatomical structures of the object;

calculating a parameter value for each calculated at least one biometric parameter; and calculate a cross-correlation of the calculated parameter values.

13. The method of claim 12, wherein calculating at least one biometric parameter is based on a measurement algorithm.

14. The method of claim 12, wherein the plurality of different measurements of the anatomical structure: (i) evaluate different biometric measures of the object; (ii) are performed based on different measurement algorithms; or (iii) are performed based on segmentation data derived from different 3D ultrasound data sets.

15. The method of claim 12, further comprising the step of:

estimating an accuracy of the calculation of the at least one biometric parameter of each of the plurality of different measurements if the calculated cross-correlation is above a predefined correlation threshold, or calculating a further parameter value of the at least one biometric parameter of each of the plurality of different measurements if the calculated cross-correlation is below a predefined correlation threshold.

16. Ultrasound imaging apparatus for imaging an object, comprising:

a graphical user interface configured to display ultrasound image data, and an ultrasound diagnosis apparatus as claimed in claim 1 for analyzing the object, wherein the graphical user interface is adapted to display the calculation results of the at least one biometric parameter.

17. An ultrasound diagnosis apparatus, comprising:

an ultrasound data interface configured to receive 3D ultrasound data about an object; and a processor configured to: (i) provide 2D ultrasound planes based on the 3D ultrasound data, (ii) segment an anatomical structure of the object in the 2D ultrasound planes and for providing segmentation data of the anatomical structure; (iii) measure the anatomical structure of the object using the segmentation data of the anatomical structure to generate a plurality of different measurements of the anatomical structure; (iv) calculate at least one biometric parameter of each of the plurality of different measurements of the anatomical structure; (v) calculate a parameter value of each of the at least one biometric parameters; and (vi) calculate a cross-correlation of the parameter values.

18. The ultrasound diagnosis apparatus of claim 17, wherein the processor is configured to calculate the at least one biometric parameter of each of the plurality of different measurements of the anatomical structure based on a measurement algorithm.

19. The ultrasound diagnosis apparatus of claim 17, wherein the plurality of different measurements of the anatomical structure: (i) evaluate different biometric measures of the object; (ii) are performed based on different measurement algorithms; or (iii) are performed based on segmentation data derived from different 3D ultrasound data sets.

20. The ultrasound diagnosis apparatus of claim 17, wherein the processor is configured to estimate an accuracy of the calculation of the at least one biometric parameter of each of the plurality of different measurements of the anatomical structure if the calculated cross-correlation is above a predefined correlation threshold; and wherein the processor is configured to calculate a further parameter value of the at least one biometric parameter of each of the plurality of different measurements of the anatomical structure if the calculated cross-correlation is below a predefined correlation threshold.

* * * * *